The following figure shows

United States Patent

Manzatu et al.

[11] Patent Number: 5,846,397
[45] Date of Patent: Dec. 8, 1998

[54] PLANT AND PROCESS FOR ACHIEVING STRUCTURED WATERS OF THE "I" TYPE-INHIBITIVELY ACTIVATED AND "S" TYPE STIMULATIVELY ACTIVATED

[75] Inventors: Ioan Manzatu; Vasile Ionita-Manzatu, both of Bucharest, Romania

[73] Assignee: S. C. Tehman, Bucharest, Romania

[21] Appl. No.: 793,127

[22] PCT Filed: Aug. 15, 1995

[86] PCT No.: PCT/RO95/00010

§ 371 Date: Feb. 10, 1997

§ 102(e) Date: Feb. 10, 1997

[87] PCT Pub. No.: WO96/06048

PCT Pub. Date: Feb. 29, 1996

[30] Foreign Application Priority Data

Aug. 22, 1994 [RO] Romania ............................... 94-01403

[51] Int. Cl.[6] .................................................. C02F 1/461
[52] U.S. Cl. ........................... 205/748; 204/257; 204/263
[58] Field of Search .................................... 204/257, 263; 205/748

[56] References Cited

U.S. PATENT DOCUMENTS 5,340,458  8/1994  Koizumi .................................. 204/257
5,474,662  12/1995  Miyamae ................................ 204/257

FOREIGN PATENT DOCUMENTS 0 396 107 A2  11/1990  European Pat. Off. .
34 21 459 A1  12/1984  Germany .
   2 062 914   6/1981  United Kingdom .
WO 83/02606   8/1983  WIPO .
WO 90/15779  12/1990  WIPO .

Primary Examiner—Arlin S. Phasge
Attorney, Agent, or Firm—Herbert Dubno; Jonathan Myers

[57] ABSTRACT

An apparatus is disclosed for obtaining inhibitively active "I" water and stimulatively activated "S" water which comprises:

a parallelipipedic column having an open top;

a support for said column;

a cover closing said top of said column;

at least one electrode assembly in said column and including:

a pair of spaced apart mutually parallel porous membranes defining between inner surfaces thereof a supply space receiving water to be separated into inhibitively activated "I" water and stimulatively activated "S" water, respective porous electrodes spaced from outer surfaces of said membranes and parallel thereto, and a respective spacer between each of said electrodes and the respective outer surface whereby water flows outwardly from said supply space through said membranes and said electrodes;

means for electrically connecting one of said electrodes as a positive electrode and the other of said electrodes as a negative electrode;

means in said column for forming a first storage space adjacent said positive electrode for collecting said I-water and a second storage space adjacent said negative electrode for collecting said S-water; and respective outlets formed in said column and communicating with said storage spaces for respectively discharging said I-water and said S-water.

6 Claims, 1 Drawing Sheet

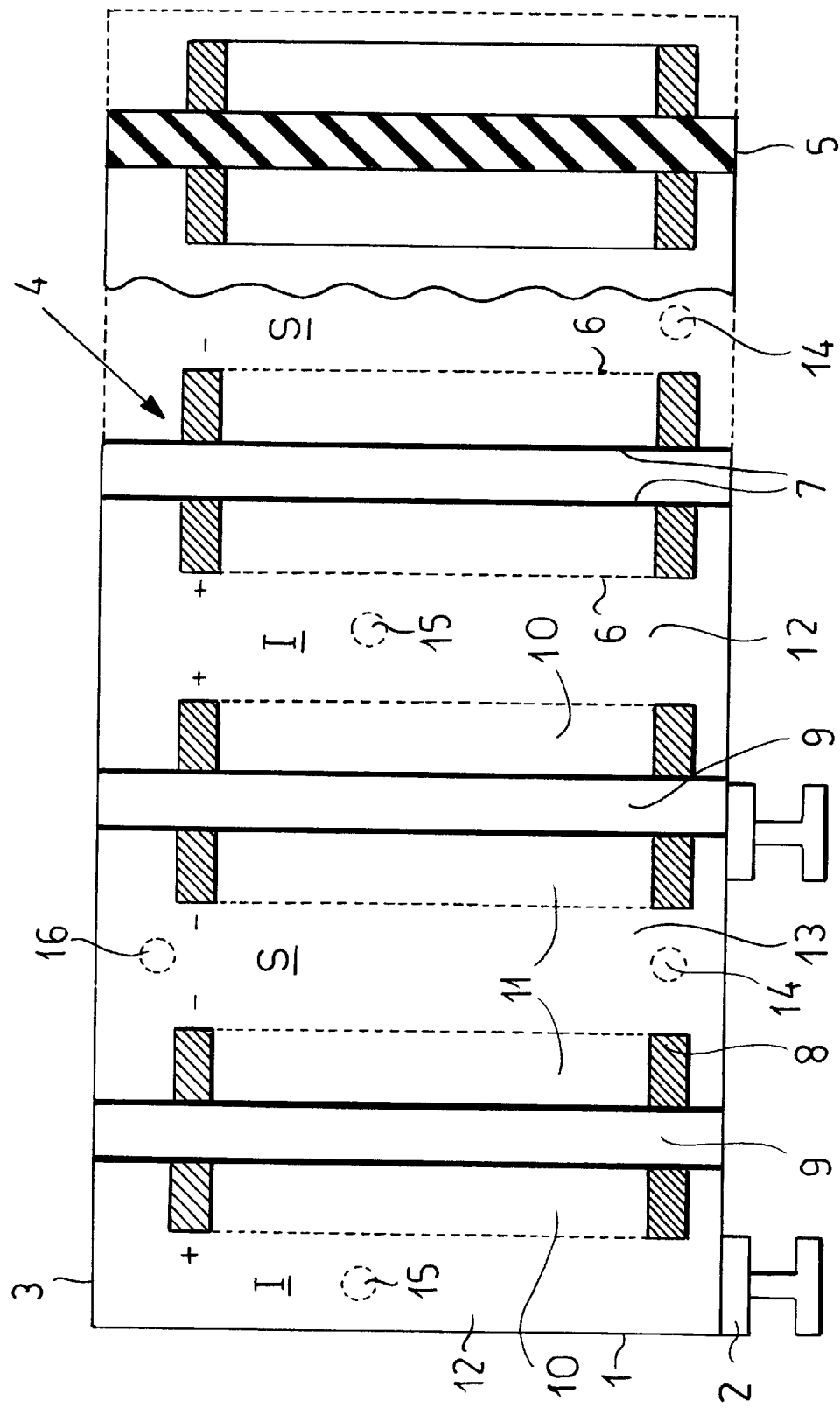

PLANT AND PROCESS FOR ACHIEVING STRUCTURED WATERS OF THE "I" TYPE-INHIBITIVELY ACTIVATED AND "S" TYPE STIMULATIVELY ACTIVATED

This application is 371 of PCT/RO95/00010 filed Aug. 15, 1995.

TECHNICAL FIELD

The invention deals with the plant and process for achieving structured waters of the "I" type-inhibitively activated and "S" type-stimulatively activated, applicable in medicine, biology, electrochemistry, bioenergetics, pharmaceutical an cosmetic industry, agriculture etc.

This invention reports on a plant and related process intended to structure (activate) the tap water, by its separation—under electric field—into two components, namely: the "I"type-inhibitively activated water for biosynthesis processes, that uses the inductive dextrogyre components and the "S" type-stymulatively activated water for biosynthesis process, that uses the inductive levogyre components.

BACKGROUND ART

In the last decades, various studies were performed and several assumptions were made on the properties and molecular structure of the water.

A large number of authors: J. D. Bernal and R. B. Fowler "Trends in Biochemical Science" vol. 8, no. 1. page. 20, 1983,25 Paula T. Beall "The Sciences", vol. 21, page.6, 1981, Frank H. Stillinger "Science", vol. 209, no. 4455, page. 451, 1980, H. S. Frank and W. J. Wen "Proc. R. Soc. London", seria A 247, page. 481, 1980, F. M. Richards and T. Richmond "Ciba Symposium", 60, page.23, 1978, F. Franks "A Treatise on Water", vol. 1–7, Ed. Plenum, New York, 1985, drew the conclusion that the water gets another structure and other functions as soon as it reaches within or on the surface of proteins and especially inside the living cells. One can assume that inside the living cells membrane or within them, some mechanisms are included meant to structure the water in a manner required from the metabolic and biosynthesis processes specific to the living cells.

At the same time, the attempts of many other authors are worth mentioning, for finding processes by which they can achieve polymolecular structures of the structured waters of the "A"-acid and "B"-basic type, respectively. Thus, the plant and process for achieving the "B" type-basic biologically stimulative water, according to the Romanian Patent no. 88053 and also the plant and process for achieving the "A" type-acid biologically inhibitive water, according to the Romanian Patent no. 88054, consist in a cylindrical and parallelipipedic column within which two cylindrical or three lamellar electrodes are concentrically or parallel placed, made of noble materials such as platinum, separated from one another by one or two identical cylindrical or lamellar porous membranes placed so that make a central compartment for circulating the input water meant to upstream structuring and two side compartments for gathering the acid and basic structured water, respectively. The process for achieving the biologically antagonistic acid water and biologically stimulative basic one, respectively, implies that the water purified by removing ions and other organic structures, with a conductivity ranged between 1 and 80 $\mu$S, undergoes the simultaneous action of some cooperative fields of electrostatic type, having values ranged between 1 and 2,500 V of radio frequency type with values between 50 Hz and 1 GHz, and of ultrasound type having values between 50 Hz and 1.5 MHz, so that an unaltered common water fraction and two fractions having different polymolecular structures with pH=1–5 and 7–12, respectively, are obtained The disadvantages of these plants are the following:
use of tap water—for structuring—purified by distillation or by ion exchanger, up to conductivities ranged between 1 and 80 $\mu$S;
use of three spaces in the structuring unit, namely: one for the "A" acid structured water, another for "B"-basic water and a central space named neutral, from where the water leaves with unaltered pH;
the extremely low efficiency, that is 7 l/h of "A" water and 7 l/h of "B" water can be achieved at most from 140 l/h of the input purified water, meaning that 126 l/h of purified water are lost (data from experiments);
use of noble metal electrodes, especially platinum, very expensive and unavailable for users;
the power consumption per liter of "A" or "B" structured water is about 500 Wh/l;

DISCLOSURE OF INVENTION

The "I"-inhibitively activated water is a strong blocker of the biosynthesis processes where the levogyre components are used. This phenomenon is due to the fact that any coupling of dextrogyre structures from the "I" type-inhibitively activated water with levogyre-type biosynthesis proteins, is of dextrogyre type.

Since the polymolecular structures of "I" type-inhibitively activated water are dextrogyre, they act on the inhibitive elements, by blocking some factors, especially the proteic ones, needed to replicate DNA, to progress RNA towards the ribosomes of the protein synthesis process, beginning with the RNA-amino acid-like couplings and proceeding with the protein synthesis initiation at the level of polisome, peptide elongation, their release, etc. Given the blocking properties of some cell multiplying processes, the polymolecular structures of "I" tipe-inhibitively activated water prove themselves strong brakes or blockers of those mechanisms.

The "S" type-stimulatively activated water acts as a stimulative factor in all important mechanisms for information transmission and protein synthesis.

In understanding the biosynthesis mechanisms one should realize that the "I" type-inhibitively and "S" type-stimulatively activated aqueous structures are energy carriers by their very shaping process (left screw and right screw, respectively).

The plant for achieving the structured waters of the "I"type-inhibitely activated and "S" type-stimulatively activated—removes, according to this invention, all the above mentioned disadvantages in that it uses one or several serial structuring cells placed in a chemically neutral paralielipipedic column, propped on a four-legged support and enclosed on top by a cover; each structuring cell consists of a pair of activators and working spaces, namely: two spaces for tap water supply, two spaces for generating the "I" type-inhibitively activated water, two spaces for generating the "S" type, two spaces for gathering and disposal of "I"-inhibitively activated water and a space for gathering and disposal of "S"-stimulatively activated water; the activators, tightly placed by a gasket in the parallelipipedic column, are made of two inox stainless lamellar electrodes each, through which the water passes (net), placed on one and the other sides of a sandwich of chemically inert, porous membranes, resistant to solutions having pH=2–14, by means of some plastic spacing pieces; the positive electrode in the space for gathering and disposal of the "I" type-inhibitively activated water of the first structuring cell is connected to the positive pole of a d.c. generator with a voltage ranged between 40–800 V, and the negative electrode of the last structuring cell being connected to the negative pole of the d.c. generator, the number of structuring cells depending on the value of the electrostatic field between electrodes, needed to perform the structuring process, so that the tap water entering the connecting pieces placed at the bottom of the spaces, gets up in the supply spaces and, due to its passage through membranes also fills all the spaces and under the influence of electrostatic field developed between the electrodes, undergoes the structuring process so that the structures having the general formula $R^-H^+$ where $R^-$ is a polymeric radical, migrate towards the positive electrodes in the spaces for producing the "I"-inhibitively activated water, being gathered as the "I" type inhibitively activated water in the gathering spaces and disposed through the connecting pieces placed in the middle of the parallelipipedic column, and the structures having the general formula $R^-(OH)^-_n$ migrate towards the negative electrodes in the spaces for producing the "S"-stimulatively activated water, being gathered under the form of stimulatively activated water in the spaces and disposed through the connecting pieces placed on top of the parallelipipedic column.

The process for achieving the structured waters of the "I" type-inhibitively activated and "S" type-stimulatively activated, according to the invention, using the above mentioned plant, consists in the use—for structuring—of the tap water having a conductivity ranged between 250–450 $\mu$S/cm and pH between 7–7.50 with a flow rate of 120 l/h, the value of the electrostatic field between electrodes being nearly 100 V, the water enters the parallelipipedic column with a volume of about 100 l, which contains only one structuring cell with two activators; in the spaces for producing the "S"-type-stimulatively activated water, a complex process occurs by which, as a result of the existence of an electrostatic field, there are provided some arrangements, polarizations and the energy needed for binding of the water molecules—by hydrogen and hydroxyl bridges—in polymolecular aggregates with radicals ($R^+$), resulting in the "S" type stimulatively activated water with pH ranged between 10–12 and the conductivity between 600–2,500 $\mu$S/cm which is gathered in the respective spaces and disposed through the connecting pieces with a flow rate of about 60 l/h, in the spaces for producing the "I"-inhibitively activated water, a complex process occurs too, by which, as a result of the electrostatic field between electrodes, there are provided arrangements, polarizations and the energy needed to bind—by hydrogen bonds of the water molecules in polymolecular aggregates with radical ($R^-$), the "I"-inhibitively activated water being resulted with pH between 2–4 and conductivity between 500–3,000 $\mu$S/cm, which is gathered in the respective space and disposed with a flow rate of about 60 l/h through the connecting pieces; for "n" structuring cells, the value of electrostatic field is about n·100 V, the input flow rate being nearly n·120 l/h and the parallelipipedic column volume n·100 l.

The advantages of the invention are the following:
use of tap water for structuring, instead of distillation—purified tap water, followed by ion inclusion;
use of food inox electrodes instead of noble metal electrodes, such as platinum;
decrease in the unstructured water loss to zero, by eliminating the neutral central space and its replacing by the space for gathering the "S" type-stimulatively activated water;
produces "I" type-inhibitively and "S" type-stimulatively activated waters with a very high efficiency: 60 l/h of "I" type inhibitively and 60 l/h of "S" type-stimulatively activated water are obtained from 120 l/h input tap water;
reduction in the power consumption per liter of "S" type-inhibitively and "S" type-stimulatively activated water from about 500 W/l to 30 W/l.

This invention develops a plant for producing "I" type-inhibitively and "S"-stimulatively activated waters with the related process for their achievement, with a plainly higher structuring efficiency using low cost materials.

BRIEF DESCRIPTION OF DRAWINGS

FIG. 1 represents a cross section and view of plant.

BEST MODE FOR CARRYING OUT THE INVENTION

Further on, an example is given, concerning the plant development according to the invention and the FIG. 1.

The plant for producing the "I" type-inhibitively and "S" type-stimulatively activated waters, consists of a plastic, chemically neutral parallelipipedic column 1, propped on a four-legged support 2 and enclosed on top by a cover 3, which contains only one structuring cell made of two activators 4 and nine working spaces: two supply spaces 9, two spaces 10 for producing "I" type-inhibitively activated water, two spaces 11 for producing "S" type-stimulatively activated water, two spaces 12 for gathering and disposal of "I" type-inhibitively activated water and a space 13 for gathering and disposal of "S" type-stimulatively activated water.

Each activator tightly placed through a gasket 5 in the parallelipipedic column 1, is made of two inox lamellar electrodes 6 through which the water can pass, places on one and the other sides of a sandwich of woven, chemically inert membranes 7, resistant to solutions with pH=2–14, through some plastic spacing pieces 8. The membrane sandwich 7 of each activator 4 make the supply spaces 9 with the tap water entering through the connecting piece 14 and feeds the space 10, 11, 12 and 13, the "I" type inhibitively activated water is disposed through the connecting pieces 15 and the "S" type-stimulatively activated water is disposed through the connecting piece 16. The water structuring compartments 10 and 11 and the spaces 12 for gathering and disposal of the "I" type-inhibitively activated water and the space 13 for gathering and disposal of "S"-type stimulatively activated water are enclosed on top by a plastic cover 3 where there are the holes for connecting the electrodes 6 according to the polarities at the terminals (+) and (−) of the d.c. generator, not provided in FIG. 1.

Also, an example of achieving the "I" type-inhibitively and "S" type-stimulatively activated waters is given further. The tap water having a conductivity ranged between 250–450 $\mu$S and pH between 7–7.50 enters through connecting piece 14, the supply spaces 9 with a flow rate of 120 l/h feeding the spaces 10, 11, 12 and 13. In the spaces 11 for producing "s" type-stimulatively activated water, a complex process occurs, by which, as a result of the existence of an electrostatic field developed by a d.c. generator with a voltage of about 100 V, there are provided arrangements, polarizations and the needed energy for binding—by hydrogen and hydroxyl bridges of the water molecules in polymolecular aggregates with radicals (R$^+$), the "S" type-stimulatively activated water being resulted with pH ranged between 10–12 and conductivity between 600–2,500 $\mu$S/cm. The "S" type-stimulatively activated water is gathered in the space 13 and disposed with a flow rate of 60 l/h through the connecting piece 16. In the spaces 10 for producing the "I" type-inhibitively activated water, a complex process occurs too, by which, as a result of the electrostatic field developed by the d.c. generator with a voltage of about 100 V, there are provided arrangements, polarizations and the energy needed for binding—by hydrogen bridges of the water molecules in polymolecular aggregates with radicals (R$^-$), the "I" type-inhibitively activated water being resulted with a pH ranged between 2–3 and conductivity between 500–3000 $\mu$S/cm. The "I" type-inhibitively activated water is gathered in the gathering spaces 12 and disposed through the connecting pieces 15 with a flow rate of about 60 l/h.

It should be mentioned that, instead of tap water, any aqueous solution can be used.

J. D. Bernal and E. B. Fowler in "Trends in Biochemical Science" vol. 8, no. 1, pg. 20, 1983, in their theory on the water nature, showed that, as an ordering electric field is missing, an equilibrium is established in the water between the (H$_3$O)$^+$ and (OH)$^-$-like structures. If a polarized electric field passes through the water, the (H$_2$O)$^+$ and (OH$_2$)$^-$-like structures begin to move independently and the equilibrium between them, is broken. Also, many proteins such as serinprotease, contain—within their structures—stable water groups under the form of some ligand structures.

Paula T. Beall in "The Science" vol. 21, pg. 6, 1981, found, through some very sophisticated measuring techniques (spin water, a process occurring too, by which there are provided some arrangements, polarizations and the energy needed to bind the water molecules—by hydrogen bridges—in polymolecular aggregates with negative radicals R$^-$, resulting in "I"-inhibitively activated, structured water with pH between 2 and 4 and conductivity between 500–3,000 $\mu$S, which is gathered in the gathering spaces 12 and discharged with a flow rate of about n×60 l/h through the discharge connecting pieces 15.

J. D. Bernal and E. B. Fowler in "Trends in Biochemical Science" vol. 8, no. 1, pg.20, 1983, in their theory on the water nature, showed that, as long as an ordering electric field is missing, an equilibrium is established in the water between the (H$_3$O)$^+$ and (OH)$^-$-like structures. If a polarized electric field passes through the water, the (H$_2$O)$^+$ and (OH$_2$)$^-$-like structures begin to move independently and the equilibrium between them is broken. Also, many proteins such as serinprotease, contain—within their structures—stable water groups under the form of some ligand structures.

Paula T. Beall in "The Science" vol.21, pg.6,1981, found through some very sophisticated measuring techniques (spin electronic resonance, nuclear magnetic resonance, isotope diffusion, flexible electron scattering, dielectric relaxation, etc.), that the water properties and behaviour within the living cells are different from those of the outside water. In this respect, the authoress mentions that, inside the cells, the water has a longer time to maintain its structures and the degrees of freedom for movement of those water structures are highly altered, meaning their slowing. These data lead to the assumption that the water structure in the living cells differs from the water structure outside them.

Also, an exhaustive molecular theory is known on the water structure, proposed by Frank H. Stillinger, based on the latest experimental data. The author shows that the results of tie quantum mechanics studies support the idea of H. S. Frank and W. J. Wen ("Proc.R. Soc. London", series A 247, page. 481, 150) according to which, the hydrogen bonds in the water are "cooperative"-like. After forming the first hydrogen bond, the change distribution between the participating monomers is modified so that the hydrogen acceptor molecule becomes potentially a better hydrogen donor than before. Hence, the molecule is able to form the second stronger bond, due to the existence of the first bond. Similarly the proton donor has an increased capacity to accept a proton based on its already formed bond. This mutual intensification makes the molecules form chains of hydrogen bonds, with a higher average energy and an average bond length smaller than for the simple dimer.

Presumptively, the rearrangement of proteic groups by the ligand, when a compound is formed, would alter these arrangements changing the number of water molecules in the active situs. The tree hydration energy of a macromolecule is very high, nearly 150 kcal/mol of lysosomes or 2.5 Kcal/100 A$^2$ of protein area. Thus, a small alteration in the surface water arrangement is found and I. M. Richards and T. Richmond ("A Treatise on Water", vol. 1–7, Ed. Planum, New York, 1985),conclude that special water properties must exist associated with an active situs. Difference between hydration of a protein and of a nucleic acid seems to be entirely in the last step, that is in the completion of the hydration process, after saturating the charged and polar situses. The nucleic acids can require more water, since they have a water multilayer or a much denser arrangement of the surface water. Study of hydration of cell membranes and organized elements is very important, considering the controversy regarding the water nature in cells. In addition to those mentioned above, the huge material on water found in the 7 volumes of Felix Franks Treatise, should be included.

INDUSTRIAL APPLICABILITY

The plant for producing the structured waters of the "I" type-inhibitively activated and "S" type-stimulatively activated—and the related process for their development can be physically developed using the classical production technologies with usual materials and low cost price and it can be installed in any factory or institute for achieving components and products used in medicine, biology, electrochemistry, bioenergetics, pharmaceutical and cosmetic industry, agriculture etc.

We claim:

1. An apparatus for obtaining inhibitively active "I" water and stimulatively activated "S" water which comprises:

a parallelipipedic column having an open top;

a support for said column;

a cover closing said top of said column;

at least one electrode assembly in said column and including:

a pair of spaced apart mutually parallel porous membranes defining between inner surfaces thereof a supply space receiving water to be separated into inhibitively activated "I" water and stimulatively activated "S" water, respective porous electrodes spaced from outer surfaces of said membranes and parallel thereto, and a respective spacer between each of said electrodes and the respective outer surface whereby water flows outwardly from said supply space through said membranes and said electrodes;

means for electrically connecting one of said electrodes as a positive electrode and the other of said electrodes as a negative electrode;

means in said column for forming a first storage space adjacent said positive electrode for collecting said I-water and a second storage space adjacent said negative electrode for collecting said S-water; and respective outlets formed in said column and communicating with said storage spaces for respectively discharging said I-water and said S-water.

2. The apparatus defined in claim 1 containing two electrode assemblies with the two respective negative electrodes adjacent to one another, a supply space located between each of said two membranes within each of said two electrode assemblies for tap water supply, two spacers for producing the inhibitively active "I" water created between the positive electrodes and their membranes, two spacers for producing the stimulatively active "S" water completed between the negative electrodes and their membranes, two spaces for gathering and disposal of the "I" type inhibitively activated water, and a space for gathering and disposal of the "S" type stimulatively activated water, said latter space located between each of the two respective negative electrodes adjacent to one another in each of the two electrode assemblies.

3. The apparatus defined in claim 1 wherein at the bottom of the supply spaces, inlets are provided for tap water supply, wherein in the middle of the two spaces for gathering and disposal of the "I" type inhibitively activated water outlets are provided for disposal of the "I" type inhibitively activated water, and wherein at the top of the space for gathering and disposal of the "S" type stimulatively activated water an outlet is provided for disposal of the "S" type stimulatively activated water.

4. The apparatus defined in claim 1 wherein the porous electrodes in the electrode assembly are net-shaped.

5. The apparatus defined in claim 1 wherein the porous electrodes in the electrode assembly are made of stainless steel.

6. A process for obtaining inhibitively active "I" water and stimulatively activated "S" water which comprises the steps of:

(a) passing tap water with a conductivity between 250 and 450 $\mu$S/cm and a pH between 7 and 7.50 through an electrode assembly which includes:
 a supply space defined by inner surfaces of a pair of spaced apart mutually parallel porous membranes,
 respective porous electrodes spaced from outer surfaces of said membranes and parallel thereto, and
 a respective spacer between each of said electrodes and the respective outer surface, whereby the tap water flows outwardly from said supply space through one of said membranes and one of said electrodes;

(b) electrically connecting one of said electrodes as a positive electrode and the other of said electrodes as a negative electrode to an external d.c. power source;

(c) forming the inhibitively active "I" water from the tap water flowing in the spacer between the outer surface of one of the porous membranes and the positive electrode;

(d) forming the stimulatively active "S" water from the tap water flowing in the spacer between the outer surface of one of the porous membranes and the negative electrode; and (e) discharging the inhibitively active "I" water and the stimulatively active "S" water.

* * * * *